US010093962B2

(12) United States Patent
Borns (10) Patent No.: US 10,093,962 B2
(45) Date of Patent: Oct. 9, 2018

(54) FAST HYBRIDIZATION FOR NEXT GENERATION SEQUENCING TARGET ENRICHMENT

(71) Applicant: Agilent Technologies, Inc., Santa Clara, CA (US)

(72) Inventor: Michael Borns, Escondido, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 221 days.

(21) Appl. No.: 14/868,961

(22) Filed: Sep. 29, 2015

(65) Prior Publication Data

US 2016/0017405 A1 Jan. 21, 2016

Related U.S. Application Data

(62) Division of application No. 14/167,513, filed on Jan. 29, 2014, now Pat. No. 9,587,268.

(51) Int. Cl.
*C12Q 1/68* (2018.01)
*C12P 19/34* (2006.01)
*C07H 21/02* (2006.01)
*C07H 21/04* (2006.01)
*C12Q 1/6806* (2018.01)
*C12Q 1/6832* (2018.01)

(52) U.S. Cl.
CPC ......... *C12Q 1/6806* (2013.01); *C12Q 1/6832* (2013.01)

(58) Field of Classification Search
USPC ......... 435/6.1, 6.11, 91.1, 183; 436/94, 501; 536/23.1, 24.3, 24.33
See application file for complete search history.

(56) References Cited

U.S. PATENT DOCUMENTS

| | | | |
|---|---|---|---|
| 4,766,064 A | 8/1988 | Williams et al. | |
| 4,886,741 A | 12/1989 | Schwartz | |
| 5,512,436 A | 4/1996 | Stone | |
| 6,706,499 B2 | 3/2004 | Mangnsson et al. | |
| 7,198,701 B2 | 4/2007 | Ueda et al. | |
| 7,867,703 B2 | 1/2011 | Sampson et al. | |
| 7,939,645 B2 | 5/2011 | Borns | |
| 7,955,795 B2 | 6/2011 | Kumar | |
| 8,158,359 B2 | 4/2012 | Leamon et al. | |
| 8,426,126 B2 | 4/2013 | Latham et al. | |
| 2005/0084881 A1 | 4/2005 | Kelley et al. | |
| 2006/0210997 A1 | 9/2006 | Myerson et al. | |
| 2008/0132694 A1 | 6/2008 | Himmelreich et al. | |
| 2008/0207960 A1 | 8/2008 | Lin et al. | |
| 2008/0226705 A1 | 9/2008 | Soltero et al. | |
| 2009/0111711 A1 | 4/2009 | Lewandowski et al. | |
| 2009/0318305 A1 | 12/2009 | Lin et al. | |
| 2010/0029498 A1 | 2/2010 | Gnirke et al. | |
| 2011/0172105 A1 | 7/2011 | Gage et al. | |
| 2013/0310260 A1 | 11/2013 | Kim et al. | |
| 2014/0234844 A1 | 8/2014 | Matthiesen | |

FOREIGN PATENT DOCUMENTS

| | | |
|---|---|---|
| CN | 1688709 A | 10/2005 |
| CN | 1697881 A | 11/2005 |
| EP | 1510577 A1 | 3/2005 |
| EP | 2865764 A1 | 4/2015 |
| WO | 2001/035100 A2 | 5/2001 |
| WO | 200200848 | 1/2002 |
| WO | 2002033126 A2 | 4/2002 |
| WO | 2006012500 A2 | 2/2006 |
| WO | 2009099602 A1 | 8/2009 |
| WO | 2011067678 A2 | 6/2011 |
| WO | 2013046033 A1 | 4/2013 |
| WO | 2013191197 A1 | 12/2013 |

OTHER PUBLICATIONS

Office Action dated Feb. 13, 2017 for Europe Patent Application No. 15152868.4.
Gouya et al., "Modulation of the Phenotype in Dominant Erythropoietic Protoporphyria by Low Expression of the Normal Ferrochelatase Allele," Am. J. Hum. Genet. (1996); 58:292-299.
Nakano et al., "Nucleic acid duplex stability: influence of base composition on cation effects," Nucleic Acids Research (1999); 27(14):2957-2965.
European Search Report dated Sep. 6, 2017 for EP Application No. 17180680.5.
Springer et al., "Shielding effect of monovalent and divalent cations on solid-phase DNA hybridization: surface plasmon resonance biosensor study," Nucleic Acids Research (2010): 38(20):7343-7351.
Grover et al., "Targeted sequence capture as a powerful tool for evolutionary analysis," American Journal of Botany (2012): 99(2):312-319.
Querfurth et al., "Creation and application of immortalized bait libraries for targeted enrichment and next-generation sequencing," BioTechniques (Jun. 2012): 52(6):375-380.
Agilent's SureSelect Target Enrichment System: bringin cost and process efficeincy to next-generation sequencing (Product Note): 8 pages (Mar. 16, 2009).
Owczarzy et al., "Predicting stability of DNA duplexes in solutions containing magnesium and monovalent cations," Biochemistry (2008): 47:5336-5353.
Stangier et al., "Target specific enrichments combined with next-generation sequencing revolutionizes the analysis of human exomes," www.gatc-biotech.com (3 pages) (Apr. 2012).
Agilent's SureSelectXT Target Enrichment System for Illumina Paired-End Sequencing Library: Illumina HiSeq and Miseq Multi-plexed Sequencing Platforms (Protocol) (Oct. 2013) Version 1.6:90 pages.
Agilent's SureselectXT2 Target Enrichment System for Illumina Multiplexed Sequencing: Featuring Pre-Capture Indexing Reagents and Protocols (Protocol) (Sep. 2013) Version D.0:78 pages.

(Continued)

*Primary Examiner* — Frank W Lu (57) ABSTRACT

The present invention relates to compositions and methods of target enrichment or selection of nucleic acids using hybridization, which can be used in, e.g., next-generation sequencing.

11 Claims, 5 Drawing Sheets

(56) References Cited

OTHER PUBLICATIONS

Ellard et al., "Practics guidelines for targeted next generation seqeuncing analysis and interpretation," Clinical Molecular Genetics Society (2012) 4 pages.
Office Action dated Mar. 4, 2016 in U.S. Appl. No. 14/167,513.
Extended European Search Report Written Opinion dated Jan. 23, 2018 for EP Application No. 17180680.5 (17 pages).
Yao et al., "Molecular-beacon-based array for sensitive DNA analysis," Analytical Biochemistry (2004); 331:216-223.

| Performance | Magnesium Buffer (B) 1 hour, 10 minutes (50 cycles) rep-1 | Magnesium Buffer (B) 1 hour, 10 minutes (50 cycles) rep-2 | Magnesium Buffer (B) 1 hour, 25 minutes (60 cycles) rep-1 | Magnesium Buffer (B) 1 hour, 25 minutes (60 cycles) rep-2 | Sodium based buffer 16 hours rep-1 | Sodium based buffer 16 hours rep-2 | Sodium based buffer 24 hours rep-1 | Sodium based buffer 24 hours rep-2 |
|---|---|---|---|---|---|---|---|---|
| % On Target | 69.64% | 70.36% | 69.87% | 70.14% | 64.29% | 64.18% | 62.58 | 62.58 |
| % Duplicate | 7.96% | 7.78% | 8.05% | 8.03% | 6.89% | 6.70% | 9.10 | 9.09 |
| Percentage of targeted bases covered by | | | | | | | | |
| 1X | 98.93% | 98.91% | 98.94% | 98.94% | 98.92% | 98.94% | 98.83 | 98.83 |
| 10X | 92.47% | 92.31% | 92.54% | 92.65% | 93.38% | 93.26% | 92.81 | 92.82 |
| 20X | 82.04% | 81.94% | 82.18% | 82.35% | 80.00% | 79.73% | 78.72 | 78.75 |

- % on target refers to the percentage of sequencing reads that map back to the sequences in the bait set library used in the hybridization.
- % duplicates refers to the reads that map to the same locations.
- Percentage of targeted bases covered by X refers to the percentage of targeted bases covered at a particular read depth.

FIG. 5

FAST HYBRIDIZATION FOR NEXT GENERATION SEQUENCING TARGET ENRICHMENT

This application is a divisional application of U.S. patent application Ser. No. 14/167,513 filed on Jan. 29, 2014, now U.S. Pat. No. 9,587,268 B2, the disclosure of which is incorporated herein by reference.

FIELD OF THE INVENTION

This invention relates to compositions and methods for rapid nucleic acid hybridization. In particular, it relates to hybridization compositions and methods for target nucleic acids enrichment and selection in next-generation sequencing.

BACKGROUND OF THE INVENTION

Nucleic acid sequencing is one of the most widely used tools in molecular biology. Development of rapid and sensitive sequencing methods utilizing automated DNA sequencers has revolutionized modern molecular biology. In particular, analysis of entire genomes of plants, viruses, bacteria, fungi, and animals is now possible with next-generation sequencing technology.

Next-generation sequencing technology has brought a high level of efficiency to the process of genome sequencing. However, despite technology advances, whole genome sequencing is still associated with huge cost and workload since the related work flows tend to be complex, time-consuming, and costly to perform. In addition, there are various technical problems for accurate sample preparation, amplification and sequencing. As a result, the goal of rapid sequencing of a genome in a short period of time has not been possible.

Next-generation sequencing carried out in connection with target enrichment of certain types of genomic DNA sequencers (e.g., exons) allows one to focus on those targets. With this targeted next-generation sequencing variation, only the genomic areas of interest are sequenced, creating process efficiencies that reduce costs and allow more samples to be analyzed per study. Reducing the amount of DNA being interrogated allows investigators to perform the experiments with more statistically relevant numbers of samples.

Various approaches for targeted enrichment are available in the art. Most commonly used techniques are based on hybrid capture, PCR, and molecular inversion probes. For large target regions, hybrid capture has been the most efficient. A main advantage of this approach is enrichment in-solution rather than on microarrays; this provides easier handling and requires less DNA. In-solution capture, such as the SureSelect Target Enrichment System™ by Agilent Technologies, Inc., often applies biotinylated RNA bait molecules transcribed from DNA template oligo libraries, which are the key components and main costs. See US 20100029498, Mertes et al., Brief Funct Genomics 10:374-386, Gnirke et al., Nat. Biotechnol. 27:182-189, and Albert et al., Nat. Methods 4:903-905.

However, targeted next-generation sequencing technology is very time-consuming. A major bottleneck and speed-limiting step for the successful implementation of the targeted next-generation sequencing technology has been in the front-end steps to selectively capture and enrich targeted exons or intron regions scattered over the genomic, mitochondria and other forms of DNA, in a rapid and cost-effective manner. Indeed, the current selective hybrid capture procedure often ranges from 16 hours to over 70 hours. See, e.g., US 20100029498 and the SureSelect Target Enrichment System™ by Agilent Technologies, Inc. As a result, it usually takes as long as 2-4 days to generate a sample that is ready to be sequenced and even loner time to complete an entire sequencing process.

Thus, there is a need for compositions and methods of rapid target enrichment or selection of nucleic acids for next generation sequencing.

SUMMARY OF INVENTION

This invention relates to novel compositions for nucleic acid hybridization, related kits, and related methods. These compositions and methods allow one to complete a target enrichment of desired genomic DNA sequencers much more quickly than conventional procedures.

In one aspect, the invention features a composition for nucleic acid hybridization (i.e., hybridization composition). The composition contains a salt of a divalent cation that has a concentration in the range from about 100 mM to about 600 mM (e.g., about 150-500 mM, 200-400 mM, 250-350 mM, 100 mM, 120 mM, 150 mM, 200 mM, 250 mM, 300 mM, 350 mM, 400 mM, 450 mM, 500 mM, 550 mM, and 600 mM) and a buffering agent. The salt and the buffering agent are present in the composition at a molar ratio ranging from about 2.5:1 to about 60:1 (e.g., 2.5:1 to 30:1, 2.5:1 to 20:1, 2.5:1 to 15:1, 10:1 to 20:1, 2.5:1 to 5:1, 2.5:1, 5:1, 8:1, 10:1, 12:1, 15:1, and 20:1). In the composition, the buffering agent can have a concentration in the range from about 10 mM to about 40 mM (e.g., 15-35 mM, 20-30 mM, 20-40 mM, 20 mM, 25 mM, 30 mM, 35, mM, and 40 mM).

The divalent cation can be selected from the group consisting of magnesium, calcium, manganese, cobalt, zinc, and cadmium. In one embodiment, the divalent cation is magnesium.

The buffering agent can be selected from the group consisting of Tris, HEPES, TAPS, Tricine, Bicine, Bis-Tris, NaOH, KOH, TES, EPPS, and MOPS. The pH value of the composition can be about 7.0-11.0, e.g., 7.5-10.0, 7.0-9.0, 7.0, 7.5, 8.0, 8.5, 9.0, 9.5, 10.0, 10.5, and 11.0.

In preferred embodiments, the composition further includes a volume-excluding/thickening agent. This volume-excluding/thickening agent can have a concentration in the range from about 0.002% to about 15% w/w. The agent can be selected from the group consisting of hydroxypropyl methyl cellulose (HPMC), hydroxyethyl methyl cellulose (HEMC), hydroxybutyl methyl cellulose hydroxypropyl cellulose, methycellulose, and hydroxyl methyl cellulose. In that case, the agent can have a concentration in the range from about 0.002% to about 0.1% w/w (e.g., about 0.002% to about 0.050%, 0.004% to 0.020%, about 0.006% to 0.012%, and about 0.006%, 0.007%, 0.008%, 0.009%, 0.010%, 0.012%, 0.015%, and 0.020%). The volume-excluding/thickening agent can also be selected from the group consisting of Dextran and polyethylene glycol (PEG). And in that case, the agent can have a concentration in the range from about 1% to about 15% w/w.

The hybridization composition can further include one or more additional agents selected from the group consisting of an RNAse inhibitor, a blocking agent, a bait nucleic acid, and a target nucleic acid. In some embodiments, the target nucleic acid can be present at a concentration of about 250-3000 ng (e.g., 500-2000 ng, and 750-1500 ng) in a 30-μl reaction, i.e., 8.3 to 100 ng/μl (e.g., 16.7-66.7 ng/μl and 25-50 ng/μl). Preferably, the volume-excluding/thickening agent and nucleic acids are present in a ratio of about 0.2 to 120 (e.g., 0.2-100, 0.2-50, 0.5-10, and 0.8-8.0).

In one embodiment of the hybridization composition, the salt is $MgCl_2$, the volume-excluding/thickening agent is HPMC, and the buffering agent is Tris, pH 8.0. Preferably, the salt has a concentration of about 308 mM; the HPMC has a concentration of about 0.00834%; and the buffering agent has a concentration of about 20 mM. The salt and the buffering agent are present in the composition at a molar ratio of about 15.4:1. The composition can be free of monovalent cation or a salt thereof.

The above-described buffer compositions can be prepared from a concentrated stock solution in order to accommodate the addition of other reagents, including targets, probes, baits, blocking agents, wetting agents, and hybridization enhancing factors, as is common practice in the field of nucleic acid hybridization reactions. Accordingly, the invention also provides a buffer concentrate for preparing a hybridization composition mentioned above. The buffer concentrate can be a 2-20× (e.g., 3-15×, 4-10×, 2×, 3×, 4×, 5×, 10×, 15×, and 20×) stock so that dilution by a factor ranging from 2-fold to 20-fold (e.g., 3-15 folds, 4-10 folds, 2 folds, 3 folds, 4 folds, 5 folds, 10 folds, 15 folds, and 20 folds) yields the hybridization composition mentioned above. In a preferred embodiment, the buffer concentrate is a 5× stock and a dilution by a factor of 5-fold yields the hybridization composition mentioned above.

Also provided is a kit containing the above-mentioned buffer concentrate or hybridization composition, and a suitable packaging material therefor.

As disclosed herein, the hybridization composition can be used for nucleic acid hybridization of a target nucleic acid and a bait nucleic acid. Accordingly, the invention provides a method for nucleic acid hybridization of a target nucleic acid and a bait nucleic acid. For example, the method includes the following steps: contacting a target nucleic acid and a bait nucleic acid with the above-mentioned composition to form a hybridization mixture; denaturing the hybridization mixture at a first temperature for a first period of time (e.g., at 95° C. for 2-30 minutes, such as 2, 5, 10, 15, 20, 25, or 30 minutes); blocking the mixture at a second temperature for a second period of time (e.g., at 65° C. for 5-30 minutes, such as 5, 10, 15, 20, 25, or 30 minutes); incubating the mixture (i) at a third temperature for a third period of time and then (ii) at a fourth temperature for a fourth period of time, and repeating the incubating step for one or more times. In one embodiment, the method further includes, after the repeating step, holding the mixture at a fifth temperature (e.g., 65° C.).

The bait nucleic acid can have a RNA or DNA sequence. The target nucleic acid can have a genomic DNA nucleic acid of interest. In one embodiment, the target nucleic acid and the bait nucleic acid are not attached or affixed to a support. That is, the corresponding hybridization is in-solution hybridization.

In the method, the incubating step can be carried out for any number of cycles depending on users' assay designs, timetables, and purposes. Suitable examples of the cycle number include 20-100 times, 30-80 times, 40-70 times, and 50-60 times.

In the incubating step, the third temperature and the fourth temperature can be different or the same. If the two temperatures are different (e.g., 65° C. and 37° C.), the time durations at the two temperatures can be, for example, 1 minute and 3 seconds, respectively. Depending on the number of cycles, the incubating step and repeating step can range from 25 minutes to 3 hours or less (e.g., 25 minutes, 26, minutes, 30 minutes, 1 hour, 1.5 hours, 2 hours, and 2.5 hours). If the third temperature and the fourth temperature are the same, the time duration for the incubating step and repeating step should be longer, such as about 1-4 hours.

The details of one or more embodiments of the invention are set forth in the description below. Other features, objectives, and advantages of the invention will be apparent from the description and from the claims.

DETAILED DESCRIPTION OF THE INVENTION

This invention is based, at least in part, on an unexpected discovery that a buffer with a very high concentration of divalent cation salt allows one to capture and enrich fragmented genomic DNA via in-solution hybridization much more rapidly than conventional hybridization buffers. It is also based on an unexpected discovery that a hybridization conducted by repeatedly subjecting a hybridization mixture to two different temperatures also allows one to capture and enrich fragmented genomic DNA much more rapidly than conventional hybridization reactions which are carried out at one constant temperature.

1. COMPOSITIONS

In one aspect, the invention provides a composition or buffer for nucleic acid hybridization. The hybridization composition or buffer contains a salt of a divalent cation that has a concentration in the range from about 100 mM to about 600 mM (e.g., about 150-500 mM, 200-400 mM, 250-350 mM, 100 mM, 120 mM, 150 mM, 200 mM, 250 mM, 300 mM, 350 mM, 400 mM, 450 mM, 500 mM, 550 mM, and 600 mM), a volume-excluding/thickening agent, and a buffering agent. Various divalent cation salts, volume-excluding/thickening agents, and buffering agents can be used. The salt and the buffering agent are present in a molar ratio ranging from about 2.5:1 to about 60:1 (e.g., 2.5:1 to 30:1, 2.5:1 to 15:1, 2.5:1 to 5:1, 2.5:1, 5:1, 8:1, 10:1, 12:1, 15:1, and 20:1).

Salts

The buffer compositions according to the invention contain salts of divalent cations with higher than conventional concentrations for nucleic acid hybridization. Conventional hybridization solutions and processes for hybridization are described in J. Sambrook, E. F. Fritsch, T. Maniatis, Molecular Cloning: A Laboratory Manual, Cold Spring Harbor Laboratory Press, Cold Spring Harbor, 2nd Ed., 1989, vol. 1-3, incorporated herein by reference. Generally, conditions for conventional hybridization include (1) high ionic strength solution, (2) at a controlled temperature, and (3) in the presence of carrier DNA and surfactants and chelators of divalent cations.

Generally, conventional nucleic acid hybridization buffers (such as the Saline-Sodium Citrate (SSC) buffer and the Saline-Sodium Phosphate-EDTA (SSPE) buffer) are sodium-based and usually do not contain divalent cations, such as magnesium. Some buffers, such as SSPE, even contain chelating agents (such as EDTA) to sequester divalent cation ions derived from test samples or other sources so that such divalent cation ions, if any remain in solution, exhibit diminished reactivity. Although some literatures note magnesium can be efficient in nucleic acid duplex stabilization during hybridization, magnesium, if used in hybridization reactions, are usually used at 15 mM or lower so as to reduce non-specific hybridization reactions. See. e.g., Springer et al., Nucleic Acids Res. 2010 November; 38(20): 7343-51.

In fact, it was known in the art that magnesium affects the annealing of oligonucleotides to template DNAs by stabilizing their interactions and therefore increase non-specific annealing and produce undesirable products. When non-specific amplification occurs, $Mg^{2+}$ usually needs to be lowered or EDTA can be added to chelate $Mg^{2+}$ to increase the accuracy and specificity of the amplification. See, e.g., U.S. Pat. No. 7,939,645. As disclosed herein, it was unexpected that salts of divalent cations at high concentrations can be used successfully to capture and enrich fragmented genomic DNA via nucleic acid hybridization without sacrificing specificity.

As used herein, a "salt" refers to an ionic compound composed of cations and anions so that the product is neutral. Divalent cation salts useful in the instant invention include, but are not limited to salts of magnesium, calcium, manganese, cobalt, zinc, and cadmium. The salts can also include the bicarbonate, sulfate, chloride, carbonate, nitrate, nitrite, bromide, citrate, acetate, cyanide, oxide or phosphate salt of a divalent cation known to those of skill in the art. More preferably, the salt is magnesium chloride ($MgCl_2$), magnesium sulfate ($MgSO_4$), or magnesium nitrate ($Mg(NO_3)_2$). In addition, a salt useful in the invention can include a mixture or blend of mineral salts. Blends of mineral salts that can be used in the invention include any combination of $MgCl_2$, $MgSO_4$, and $Mg(NO_3)_2$. The salts may be used according to the invention at a concentration in the range of about 10 to 40 mM, preferably in the range of 15-25 mM, such as 20 mM.

As used herein, the term "hybridization" or "binding" refers to the pairing of complementary (including partially complementary) polynucleotide strands. Hybridization and the strength of hybridization (e.g., the strength of the association between polynucleotide strands) is impacted by many factors well known in the art including the degree of complementarity between the polynucleotides, stringency of the conditions involved affected by such conditions as the concentration of salts, the melting temperature (Tm) of the formed hybrid, the presence of other components, the molarity of the hybridizing strands and the G:C content of the polynucleotide strands. When one polynucleotide is said to "hybridize" to another polynucleotide, it means that there is some complementarity between the two polynucleotides or that the two polynucleotides form a hybrid under high stringency conditions. When one polynucleotide is said to not hybridize to another polynucleotide, it means that there is no sequence complementarity between the two polynucleotides or that no hybrid forms between the two polynucleotides at a high stringency condition.

As used herein, the term "complementary" refers to the concept of sequence complementarity between regions of two polynucleotide strands or between two regions of the same polynucleotide strand. It is known that an adenine base of a first polynucleotide region is capable of forming specific hydrogen bonds ("base pairing") with a base of a second polynucleotide region which is antiparallel to the first region if the base is thymine or uracil. Similarly, it is known that a cytosine base of a first polynucleotide strand is capable of base pairing with a base of a second polynucleotide strand which is antiparallel to the first strand if the base is guanine. A first region of a polynucleotide is complementary to a second region of the same or a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Complementary" refers to a first polynucleotide that is 100% or "fully" complementary to a second polynucleotide and thus forms a base pair at every nucleotide position. "Complementary" also refers to a first polynucleotide that is not 100% complementary (e.g., 90%, or 80% or 70% complementary) contains mismatched nucleotides at one or more nucleotide positions. In one embodiment, two complementary polynucleotides are capable of hybridizing to each other under high stringency hybridization conditions. For example, for membrane hybridization (e.g., Northern hybridization), high stringency hybridization conditions are defined as incubation with a radiolabeled probe in 5×SSC, 5×Denhardt's solution, 1% SDS at 65° C. Stringent washes for membrane hybridization are performed as follows: the membrane is washed at room temperature in 2×SSC/0.1% SDS and at 65° C. in 0.2×SSC/0.1% SDS, 10 minutes per wash, and exposed to film.

A hybridization assay, in embodiments, can take anywhere from about less than 1 hour (e.g., about 25 minutes) to 8 hours to complete, depending on at least the type and complexity of the hybridization experiment. By "complete", it is meant that a desired amount of hybridization of the target nucleic acid material is achieved, which is both user and target material dependent. As shown in the examples below, the present method and composition perform well where conventional hybridization parameters fail, for example, at a hybridization time of about 1 hour. The present method and composition perform particularly well for hybridizations taking at least 25 minutes (e.g., 1-3 hours) to complete, and more particularly, for hybridizations taking between about 1-2 hours.

Volume-Excluding/Thickening Agents

The buffer compositions according to the invention contain a volume-excluding/thickening agent. As used herein, a "volume-excluding/thickening agent" refers to an inert, viscoelastic agent that has good ability to attract and hold water molecules from the surrounding environment. Due to this water attracting-holding ability, the agent is capable of artificially increasing the concentrations of available nucleic acids and probes/baits in a hybridization solution and saturating non-specific binding sites, thereby increasing hybridization efficiency.

Preferably, the agent is a viscoelastic high-molecular weight polymer that is soluble in an aqueous solution and exhibits a thermal gelation property. That is, when the solution heats up to a specific critical temperature, the solution congeals into a non-flowable but semi-flexible mass. Typically, this specific congealing temperature is inversely related to the solution concentration of such an agent. With these characteristics, the agent exhibits two different viscoelastic states at two different temperatures. Accordingly, when it is included in a hybridization solution and used in a two-temperature (e.g., 65° C. and 37° C.) cycling incubation hybridization, the agent provides two different hybridization environments to target nucleic acids and capture probes/baits.

These two viscoelastic states coupled with the convection movement caused by the repeated changes in the hybridization temperature greatly increase the chance and probability for a capture probe/bait to encounter with its specific target nucleic acid, thereby increasing specific hybridization and forming specific target-probe/bait duplexes. In addition, the "volume-excluding" effect of the agent further enhances the efficiency by artificially increasing the concentrations of available nucleic acids and probes/baits in a hybridization solution. Also contributing to the efficiency are the high concentration divalent cations, which stabilize the specific target-probe/bait duplexes.

Various excipients and tableting ingredients used in pharmaceutical products have these characteristics. They therefore can be used as a volume-excluding/thickening agent in the buffer compositions according to the invention. Examples of the volume-excluding/thickening agent include methylcellulose and its derivatives such as hydroxypropyl methyl cellulose (HPMC), hydroxyethyl methyl cellulose (HEMC), hydroxybutyl methyl celluloses, hydroxypropyl cellulose, methycellulose, and hydroxyl methyl cellulose.

Buffering Agents

The buffer composition of this invention contains a buffering agent. The pH of the present compositions can be controlled within the ranges of from about 6.0 to about 11.0, e.g., from about 7 to about 9, from about 7.5 to about 8.5, or about 8.0. The buffering agent can be any organic or inorganic, acid or base, and alkali metal salts thereof, having at least one pKa value and/or pKb value of from about 6.0 to about 11.0. Buffering agents may have more than one pKa value and/or pKb value. A buffering agent can have at least one of its pKa values and/or pKb values within the indicated ranges.

Various buffering agents are known in the art. One skilled in the art in view of the disclosure herein could select a suitable buffering agent and design a buffer composition of this invention tailored to his or her own assays. In some examples, the buffering agent can be tris(hydroxymethyl) aminomethane) (Tris or THAM), 4-(2-hydroxyethyl)-1-piperazineethanesulfonic acid (HEPES), N-cyclohexyl-3-aminopropanesulfonic acid (CAPS), 2-(N-morpholino) ethanesulfonic acid (MES), 3-(N-morpholino) propanesulfonic acid, (MOPS), 3-[4-(2-Hydroxyethyl)-1-piperazinyl]propanesulfonic acid (HEPPS or EPPS), and others of the so-called "Good's" buffers. See, e.g., Good et al., 1966, Biochemistry 5 (2): 467-477; Good et al., 1972, Methods Enzymol. 24: 53-68; and Ferguson et al., 1980, Anal. Biochem. 104: 300-310. Additional examples include 3-{[tris(hydroxymethyl)methyl]amino}propanesulfonic acid (TAPS), N,N-bis(2-hydroxyethyl)glycine (Bicine), N-tris(hydroxymethyl)methylglycine (Tricine), 3-[N-Tris (hydroxymethyl)methylamino]-2-hydroxypropanesulfonic Acid (TAPSO), 2-{[tris(hydroxymethyl)methyl] amino}ethanesulfonic acid (TES), piperazine-N,N'-bis(2-ethanesulfonic acid) (PIPES), dimethylarsinic acid (Cacodylate), succinic acid, Bis-Tris, NaOH, and KOH.

Other suitable buffering agents can be, for example, acridine, phenylalanine, allothreonine, n-amylamine, aniline, n-allylaniline, 4-bromoaniline, 4-bromo-N,N-dimethylaniline, m-chloroaniline, p-chloroaniline, 3-chloro-N,N-dimethylaniline, 3,5-dibromoaniline, N,N-diethylaniline, N,N-dimethylaniline, N-ethylaniline, 4-fluoroaniline, N-methylaniline, 4-methylthioaniline, 3-sulfonic acid aniline, 4-sulfonic acid aniline, p-anisidine, arginine, asparagine, glycyl asparagine, DL-aspartic acid, aziridine, 2-aminoethylbenzene, benzidine, benzimidazole, 2-ethylbenzimidazole, 2-methylbenzimidazole, 2-phenylbenzimidazole, 2-aminobenzoic acid, 4-aminobenzoic acid, benzylamine, 2-aminobiphenyl, brucine, 1,4-diaminobutane, t-butylamine 4-aminobutyric acid, glycyl-2-amino-n-butyric acid, cacodylic acid, β-chlortriethylammonium-n-butyric acid, codeine, cyclohexylamine, cystine, n-decylamine, diethylamine, n-dodecaneamine, 1-ephedrine, 1-amino-3-methoxyethane, 1,2-bismethylaminoethane, 2-aminoethanol, ethylenediamine, ethylenediaminetetraacetic acid, 1-glutamic acid, α-monoethylglutamic acid, 1-glutamine, 1-glutathione, glycine, n-acetylglycine, dimethylglycine, glycylglycylglycine, leucylglycine, methylglycine, phenylglycine, N-n-propylglycine, tetraglycylglycine, glycylserine, dexadecaneamine, 1-aminoheptane, 2-aminoheptane, 2-aminohexanoic acid, DL-histidine, β-alanylhistidine, imidazol, 1-aminoindane, 2-aminoisobutyric acid, isoquinoline, 1-aminoisoquinoline, 7-hydroxyisoquinoline, 1-leucine, glycylleucine, methionine, methylamine, morphine, morpholine, 1-amino-6-hydroxynaphthalene, dimethylaminonaphthalene, α-naphthylamine, β-naphthylamine, n-methyl-α-naphthylamine, cis-neobornylamine, nicotine, n-nonylamine, octadecaneamine, octylamine, ornithine, papaverine, 3-aminopentane, valeric acid, permidine, phenanthridine, 1,10-phenanthroline, 2-ethoxyaniline, 3-ethoxyaniline, 4-ethoxyaniline, α-picoline, β-picoline, gamma-picoline, pilocarpine, piperazine, trans-2,5-dimethylpiperazine, 1-n-butylpiperidine, 1,2-dimethylpiperidine, 1-ethylpiperidine, 1-methylpiperidine, proline, hydroxyproline, 1-amino-2,2dimethylpropane, 1,2-diaminopropane, 1,3-diaminopropane, 1,2,3-triaminopropane, 3-aminopropanoic acid, pteridine, 2-amino4,6-dihydroxypteridine, 2-amino4-hydroxypteridine, 6-chloropteridine, 6-hydroxy4-methylpteridine, purine, 6-aminopurine, 2-dimethylaminopurine, 8-hydroxypurine, 2-methylpyrazine, 2-amino-4,6-dimethylpyrimidine, pyridine, 2-aldoximepyridine, 2-aminopyridine, 4-aminopyridine, 2-benzylpyridine, 2,5-diaminopyridine, 2,3-dimethylpyridine, 2,4-dimethylpyridine, 3,5-dimethylpyridine, 2-ethylpyridine, methyoxypyridine, 4-methylaminopyridine, 2,4,6-trimethylpyridine, 1,2-dimethylpyrrolidine, n-methylpyrrolidine, 5-hydroxyquinazoline, quinine, 3-quinolinol, 8-quinolinol, 8-hydroxy-5-sulfoquinoline, 6-methoxyquinoline, 2-methylquinoline, 4-methylquinoline, 5-methylquinoline, serine, strychnine, taurine, myristilamine, 2-aminothiazole, threonine, o-toluidine, m-toluidine, p-toluidine, 2,4,6-triamino-1, 2,3-triazine, tridecaneamine, trimethylamine, tryptophan, tyrosine, tyrosineamide, valine, salts thereof, and mixtures thereof. Further examples of suitable buffering agents can be found in e.g., US 20080207960 and US 20060210997, the contents of which are incorporated herein by reference. These buffers or compounds are typically and advantageously biologically inert and do not interfere with biochemical reactions.

Additional Components

The buffer compositions according to the invention can be used in various nucleic acid hybridization reaction protocols. Examples include in-solution hybridization, support-based hybridization, e.g., Northern, Southern and in situ hybridization on membranes, microarrays and cell/tissue slides. Accordingly, reaction times and temperatures, thermal cycling profiles, hybridization probe/bait sequences and concentrations, detecting agents (e.g., dyes, enzymes, radioactive isotopes, and fluorophores) for such protocols can generally be used with the buffer compositions of the present invention without alteration. The buffer compositions of the invention or related concentrated forms as discussed below therefore can include one or more additional components suitable for the protocols.

Examples of such additional components include nucleotides, nucleic acid polymerases, primers, nucleic acid templates, dyes, hybridization baits/probes, hybridization enhancing factors, blocking agents/blockers (such as carrier nucleic acids or proteins), detergents (e.g., NP40), surfactants, wetting agents, and nuclease inhibitors (e.g., RNAse inhibitors).

2. BUFFER CONCENTRATES

The buffer compositions of the invention can be prepared as concentrated stock solutions in order to accommodate the addition of other reagents, including targets, probes, baits, blocking agents, wetting agents, and hybridization enhancing factors, as is common practice in the field of nucleic acid hybridization reactions. The buffer composition can be prepared as concentrates with all components present at 2-fold to 20-fold higher concentrations, for example at 5-fold higher or 10-fold higher concentrations, than the desired final concentrations.

Examples of the buffer concentrates of the invention include a 5× stock solution comprising 1540 mM $MgCl_2.6H_2O$, 0.0417% HPMC, and 100 mM Tris (pH 8). Another example is a 2× stock solution comprising 616 mM $MgCl_2.6H_2O$, 0.01668% HPMC, and 40 mM Tris (pH 8). Yet another example is a 4× stock solution comprising 1232 mM $MgCl_2.6H_2O$, 0.03336% HPMC, and 80 mM Tris (pH 8).

3. HYBRIDIZATION METHODS

In another aspect of the present disclosure, a method of hybridizing a set of nucleic acid probes or baits with a population of target nucleic acids is provided. The method of hybridizing comprises the steps of contacting or combining the nucleic acids with a hybridization buffer composition of this invention; and incubating the resulting mixture at two hybridization temperatures, which can be different or the same.

When different, the difference between the two temperatures should be large enough (e.g., 5-40° C., 20-35° C., 20° C., 25° C., 30° C., and 35° C.) to result in convection movement of the components in the mixture, e.g., the probes/baits and target nucleic acids. In that case, the higher temperature can range from about 55° C. to about 75° C. (e.g., 60-70° C. and 65° C.) and the lower temperature can be about 30° C. to about 50° C. (e.g., 35-45° C. and 37° C.).

As mentioned above, the incubation/hybridizing time period can range, for example, from about 25 minutes to more than 8 hours. The method is particularly useful where speed and time saving are important. Preferably, the buffer agent can be selected from one or more of those disclosed above, such as Tris which has a buffering capacity within the pH range of pH 6 and 11. The cation can be provided by a salt, preferably selected from one or more of those disclosed above, and mixtures thereof. More preferably, the hybridization buffer composition can further comprise one or more additional agents, such as a volume-excluding/thickening agent, an RNAse inhibitor, a blocking agent, and a surfactant.

The hybridization method of this invention can be used in various formats of nucleic acid hybridizations, such as in-solution hybridization and such as hybridization on a solid support (e.g., Northern, Southern and in situ hybridization on membranes, microarrays and cell/tissue slides). In particular, the method is suitable for in-solution hybrid capture for target enrichment of certain types of genomic DNA sequences (e.g., exons) employed in targeted next-generation sequencing. As mentioned above, selective capture and enrichment of targeted nucleic acids has been a major bottleneck and speed-limiting step, and conventional hybridization methods fail to provide a satisfactory speedy approach. For uses in targeted next-generation sequencing, the hybridization method of this invention can be used in connection with the systems and platforms provided by Agilent Technologies, Inc., Illumina, Inc., 454 Life Sciences, Life Technologies Corporation, Affymetrix, Inc., and others.

The denaturation and blocking steps can be carried out in a standard, conventional way known in the art, but the thermo-cycling hybridization incubation step is unique. When used with the hybridization buffer of this invention, the hybridization time can be reduced to as little as about 25 minute.

The method and composition of the present invention allow one to overcome problems in the art by, for example, shortening the hybridization process and thereby speeding up the selective capture and enrichment of targeted nucleic acids. As disclosed herein, the method and the composition of the present disclosure have little bias and show good specificity, read distribution, sequence coverage, and reproducibility for next generation sequencing applications. One example of the method includes the following steps:

Step 1: Pre-warm a fast hybridization buffer of this invention at room temperature until thawed and keep at room temperature until ready to use.

Step 2: Set up blocking reactions at room temperature. Add 5 μL of a blocker mix to each 12 μL prepared DNA sample (750-1500 ng total DNA). Pipet up and down to mix. Spin down briefly. If 12 μL of the sample exceeds 1500 ng of DNA, use a smaller volume and add water to the blocking reaction for a 17 μL total volume.

Step 3: Program a SureCycler 8800 thermal cycler as shown in the table below. Start the program and hit the pause button immediately. This will heat the lid while adding the blocker mix to a pre-prepared library of genomic DNA fragments.

Step 4: Perform the thermal program on the SureCycler 8800 by hitting the play button to resume program.

| Cycling Profile: Blocking and Fast Hybridization Incubation | | |
|---|---|---|
| Step | Cycle # | Temperature and Time |
| Denaturation | 1 | 95° C. for 5 minutes |
| Blocking | 1 | 65° C. 10 minutes |

-continued

| Cycling Profile: Blocking and Fast Hybridization Incubation | | |
| --- | --- | --- |
| Step | Cycle # | Temperature and Time |
| Hybridization | 20-60 | 65° C. for 1 minute |
| | | 37° C. for 3 seconds |
| Storage | 1 | 65° C. hold |

Step 5: While the samples are incubating on the SureCycler, prepare the capture bait mix on ice.

Step 6: Dilute a SureSelect RNase Block for capture: mix 10 µL of the RNase Block (Agilent Technologies, Inc) with 30 µL of water (1 part RNase Block:3 parts water).

Step 7: Prepare the hybridization mix by adding the diluted SureSelect RNase block and SureSelect$^{XT}$ Human All Exon V5 bait (Agilent Technologies, Inc) to the room temperature fast hybridization buffer according to the table below.

| V5 Exome Hybridization Mix | |
| --- | --- |
| Component | 1 reaction |
| 1:3 Diluted RNase Block | 2 µL |
| SureSelectXT Human All Exon V5 bait | 5 µL |
| Fast Hybridization Buffer | 6 µL |
| Total | 13 µL |

Step 8: When the thermal cycle reaches the first hybridization cycle at 65° C., hit the pause button. The thermal cycler is now maintaining at 65° C. Open the thermal cycler lid and pipet 13 µL of the hybridization mix into each corresponding blocking reaction. Mix well by slowly pipetting up and down 8 to 10 times. The hybridization reaction is now 30 µL.

Step 9: Seal the wells with caps, close the lid, and hit the play button to resume the program to run the cycling hybridization profile with the hot top activated.

Step 10: Prepare magnetic beads (Dynabeads® MyOne Streptavidin T1, Invitrogen).
  1. Vigorously resuspend the Dynal (Invitrogen) magnetic beads on a vortex mixer. Dynal beads settle during storage.
  2. For each hybridization sample, add 50 µL Dynal magnetic beads to strip-tubes/96 well plate.
  3. Wash the beads:
    a. Add 200 µL SureSelect Binding buffer (Agilent Technologies, Inc).
    b. Mix the beads by pipetting up and down 10 times.
    c. Put tubes into a 96 well magnetic stand.
    d. Wait 5 minutes and remove and discard the supernatant.
    e. Repeat step a through step d for a total of 3 washes.
  4. Re-suspend the beads in 200 µL of SureSelect Binding buffer.

Step 11: Capture the hybridized DNA using streptavidin beads.
  1. After the incubation, remove the samples from the thermal cycler and briefly spin at room temperature to collect the liquid. Add the entire hybridization mixture for each sample to the corresponding washed and ready Dynal MyOneT1 Streptavidin bead solution and invert the strip-tubes/plate to mix 3 to 5 times. Incubate the hybrid-capture/bead solution on a Nutator or shaker for 30 minutes at room temperature. Make sure the samples are properly mixing in the plate.
  2. Pre-warm a wash buffer #2 at 65° C. by aliquoting out 200 µL per well in a 96 well plate (3 wells per hybridization reaction for the 3 washes). Cap the wells and incubate at 65° C. using a thermal cycler while the hybridization samples are on the nutator or shaker for 30 minutes.
  3. Briefly spin down the hybrid-capture/bead solution after 30 minutes.
  4. Separate the beads and buffer on a magnetic separator and remove the supernatant.
  5. Resuspend the beads in 200 µL wash buffer #1 by pipetting up and down 8-10 times then mix at high speed on a vortex mixer for 8 seconds.
  6. Wash the beads:
    a. Separate the beads and buffer on a 96 well magnetic stand for 1 minute and remove the supernatant.
    b. Add 200 µL A of pre-warmed wash buffer #2. Slowly pipette up and down 10 times to resuspend the beads. When pipetting the wash buffer up and down dispense the buffer directly at the pelleted beads to resuspend them faster.
    c. Cap the wells. Incubate the samples for 10 minutes at 65° C. on the thermal cycler with the hot top.
    d. Repeat steps a through step c for a total of 3 washes.
    e. Make sure the entire the wash buffer #2 has been removed.
    f. Add 23 µL nuclease free water and vortex 5 seconds to resuspend the beads and proceed to the PCR step.

Step 12: Add 25 µL of SureSelect$^{QXT}$ Herculase II Master Mix (Agilent Technologies, Inc) to each of the 23 µL samples of the Streptavidin beads bound with captured DNA.

Step 13: Add 1 µL suitable indexes, e.g., each of one of the two P5 i13 or i14 and one of the eight P7 i1-i8 (Agilent Technologies, Inc).

Step 14: Perform the thermal program on the SureCycler 8800.

Post-Capture PCR Indexing Cycling Profile

| Step | Cycle # | Temperature and Time |
| --- | --- | --- |
| Initial Denaturation | 1 | 98° C. for 2 minutes |
| Amplification | 10 | 98° C. for 30 seconds |
| | | 58° C. for 30 seconds |
| | | 72° C. for 60 seconds |
| Final extension | 1 | 72° C. for 5 minutes |
| Store | 1 | 4° C. |

Step 15: AMPureXP bead purification.
  1. Remove the Dynal MyOneT1 Streptavidin beads from the post-capture amplification reaction by placing the strip-tubes/plate on a magnetic stand for 2 minutes. Then remove the 50 µL PCR reaction to fresh strip-tubes/plate. The Dynal MyOneT1 Streptavidin beads can now be discarded.
  2. Add 60 µL of homogenous AMPure XP beads to each of the post-capture amplification reactions. Mix well by vigorous pipetting up and down 20 times. Check to make sure that the beads are evenly mixed. The beads should be homogenously one color and no layers of liquid present.
  3. Incubate the tubes for 5 minutes at room temperature.
  4. Place the tube in the 96 well magnetic stand. Wait for 5 minutes for the solution to clear. Do not disturb the tubes in the magnetic stand.

5. Carefully discard the cleared solution. Make sure to not remove any beads.
6. Continue to keep the tubes in the magnetic stand while you dispense 200 μL of 70% ethanol in each sample well.
7. Let the 70% ethanol sit for 1 minute to allow any disturbed beads to settle, then remove the ethanol. Repeat step 6 and step 7 once for a total of two washes. Make sure to remove as much of the ethanol as possible.
8. Dry the samples on a thermal cycler with the lid open at 37° C. for 1-3 minutes. Do not over dry the beads.
9. Add 25 μL of nuclease free water. Mix well by vortexing. Spin beads down briefly and incubate for 2 minutes at room temperature.
10. Place the samples on the 96 well magnetic stand for 2 minutes, until the solution is clear. Remove 25 μL of the supernatant to a fresh LoBind tube.

At this point, if there is a need, the assay can be stopped. In that case, seal the plate and store at −20° C.

Figure 2:
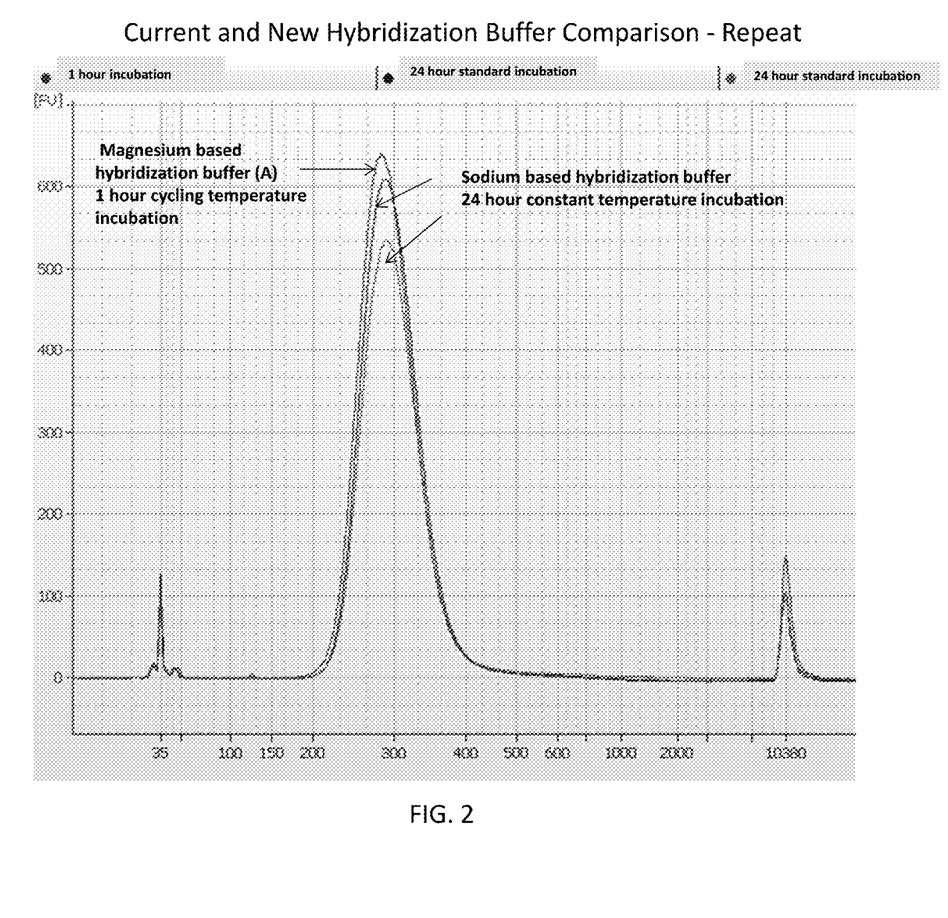
FIG. 2 is a bioanalyzer electropherogram showing DNA capture performances of a fast hybridization buffer of this invention and a conventional sodium-based hybridization buffer with a 1-hour cycling temperature incubation and 24-hour constant temperature incubations.
Figure 3:
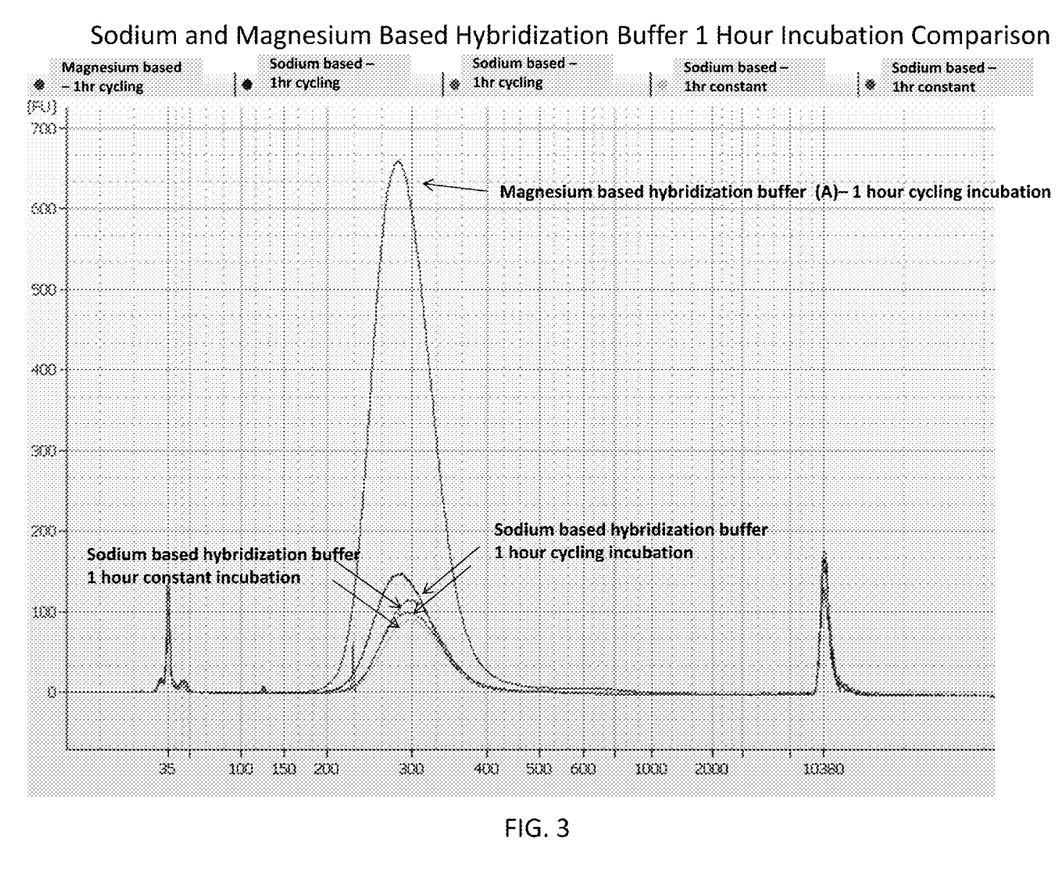
FIG. 3 is a bioanalyzer electropherogram showing DNA capture performances of a fast hybridization buffer of this invention and a conventional sodium-based hybridization buffer with 1-hour cycling temperature or 1-hour constant temperature incubations.
Figure 4:
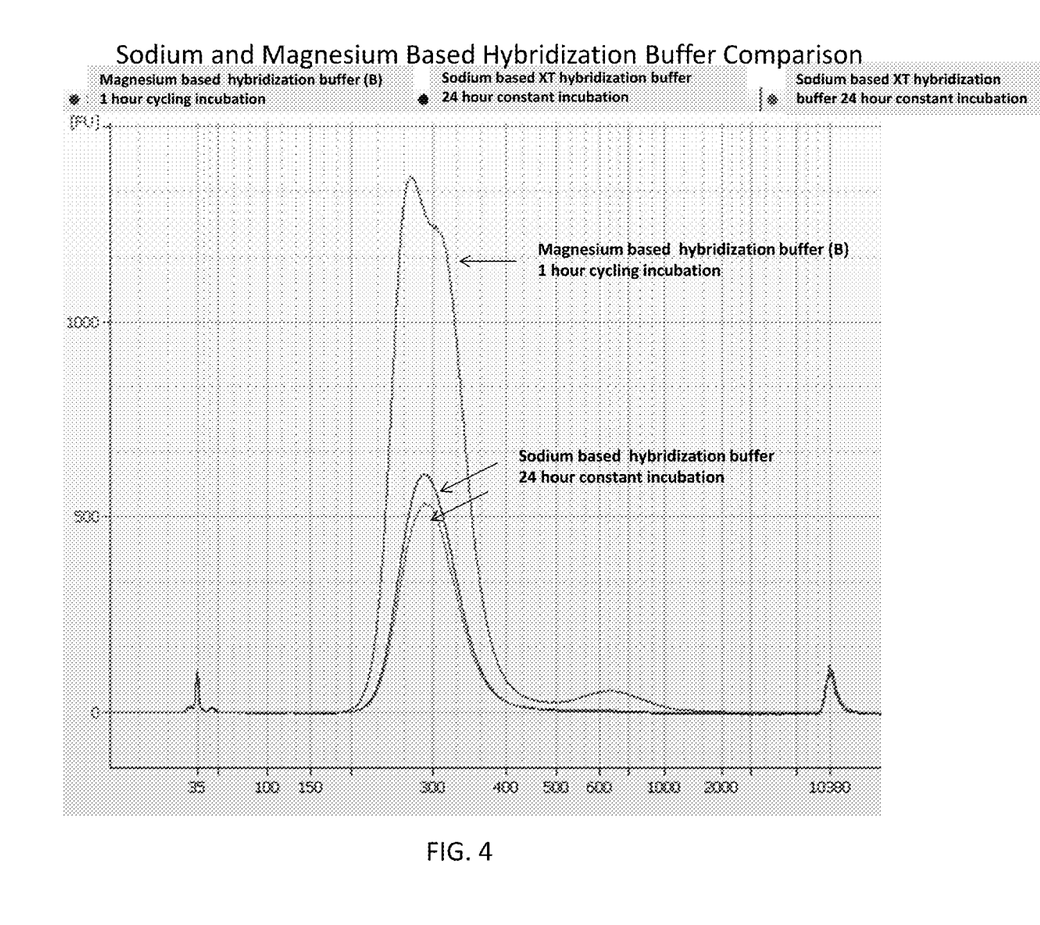
FIG. 4 is a bioanalyzer electropherogram showing comparison of a sodium-based hybridization buffer and a magnesium-based hybridization buffer.

Step 16: Access DNA samples with the 2100 Bioanalyzer High Sensitivity assay. The Bioanalyzer electropherogram profile should be similar to FIGS. 2-4.

Step 17: Pool samples for multiplexed sequencing.

The number of indexed libraries that may be multiplexed in a single sequencing lane is determined by the output specifications of the platform used, together with the amount of sequencing data required for your research design. Calculate the number of indexes that can be combined per lane, according to the capacity of your platform and the amount of sequencing data required per sample.

1. Combine the libraries such that each index-tagged sample is present in equimolar amounts in the pool. For each library, use the formula below to determine the amount of indexed sample to use.

$$\text{Volume of index} = \frac{V(f) \times C(f)}{\# \times C(i)}$$

where V(f) is the final desired volume of the pool,
C(f) is the desired final concentration of all the DNA in the pool
# is the number of indexes, and C(i) is the initial concentration of each indexed sample.
The below table shows an example of the amount of 4 index-tagged samples (of different concentrations) and low TE needed for a final volume of 20 μL at 10 nM.

| Component | V(f) | C(i) | C(f) | # | Volume to use (μL) |
|---|---|---|---|---|---|
| Sample 1 | 20 μL | 20 nM | 10 nM | 4 | 2.5 |
| Sample 2 | 20 μL | 10 nM | 10 nM | 4 | 5 |
| Sample 3 | 20 μL | 17 nM | 10 nM | 4 | 2.9 |
| Sample 4 | 20 μL | 25 nM | 10 nM | 4 | 2 |
| Low TE | | | | | 7.6 |

2. Adjust the final volume of the pooled library to the desired final concentration.

4. USES

As mentioned above, a major bottleneck and speed-limiting step for the targeted next-generation sequencing technology has been in the front-end steps to selectively capture and enrich targeted exons or targeted intron regions scattered over the genomic, mitochondria and other forms of DNA, in a rapid and cost-effective manner. The above disclosed buffer allows one to complete nucleic acid hybridization much more quickly, and thereby can be used to speed up the entire targeted next-generation sequencing.

In general, the process for capture and amplification of targeted genomic DNA fragments is as follows: (1) DNA is extracted from biological samples comprising nucleic acids; (2) The extracted DNA is fragmented by various means including mechanical, ultrasonic or enzymatic approaches; (3) Targeted DNA fragments are captured selectively by hybridizing DNA fragments with complimentary DNA and/or RNA probes or baits; (4) DNA fragments not bound to the hybridization probes are washed away first, while DNA fragments bound to the hybridization probes are eluted in the next step under appropriate conditions. (5) The captured DNA is used for downstream applications.

If a larger quantity of the captured DNA is needed, polymerase chain reactions (PCRs) are performed to amplify the captured DNA fragments by using a pair of universal primers. The universal DNA primers of specifically-designed sequences (also known as adaptors or indexing adaptors) are ligated to 5'- and 3'-ends of all DNA fragments, after either step (2) or step (4). Alternatively, the adaptors can be attached during step (2) when the extracted DNA is fragmented by an adaptor loaded transposase enzyme. Detailed procedures can be found in, e.g., the SureSelect Target Enrichment System™ marketed by Agilent Technologies, Inc. and US 20100029498. With conventional hybrid capture procedures, it generally takes at least two days to complete steps (1)-(4). Indeed, the hybridization step (i.e., step (3) above) itself usually consumes a period of time ranging from 16 hours to over 70 hours. See id.

To capture DNA fragments, the hybridization of DNA and/or RNA baits/probes takes place either on solid supporting materials or in liquid solutions. This capture step (step 3 in the above described process) is crucial for the entire process. Specificity of the capture is determined by the DNA or RNA sequences of the hybridization baits/probes. Selective capture of any desired regions of genomic and mitochondria DNA from any biological species requires a cost-effective and flexible way to carry out the hybridization steps. These DNA and/or RNA baits/probes must have sequences precisely complementary to the regions of interest in the genomic and mitochondria DNA of the biological species of interest. Capacity of the capture is determined by a combination of the number and length of different probes available for use in the hybridizations. Longer-length probes require fewer probes to cover the same DNA region for capture. Flexibility of the capture is determined by the way the probes are generated and placed on either solid supporting materials or mixed in liquid solutions. These hybridization DNA and/or RNA baits should have the overall capacity and flexibility to selectively capture all exons, or any subsets of exons, or any other desired regions of genomic, mitochondria and other forms of DNA from any biological species. The specificity, capacity, flexibility and timeliness have to be achieved in a cost-effective manner to be able to compete in the market.

As disclosed herein, the nucleic acid hybridization selective capture step can be completed within a period of time as short as about 1 hour and, as a result, the entire process for capture and amplification of targeted genomic DNA fragments can be completed within 8 hours in contrast to two or more days when using conventional approaches.

5. KITS

In still another aspect of this invention, a kit is provided that comprises the above described hybridization compositions or a buffer concentrate thereof, and instructions for performing a hybridization assay using the compositions and methods described herein. The instructions comprise the method, the composition, or both, of the present disclosure. In one embodiment, the kit further comprises a hybridization composition having one or more additional agents disclosed above, and preferably a pH maintained, for example, between pH 6.0 and 11.0, and preferably using a buffer having a useful buffering capacity in that pH range.

The compositions can be packaged in a bottle, especially a bottle that comprises a measuring closure. The measuring closure provides a convenient way to dispense the appropriate amount of the composition, especially when dispensing concentrated compositions into a more dilute solution or mixture. The bottle also preferably comprises a drain-back spout, which permits the composition to be dispensed more easily and with less waste or spillage. Non-limiting examples of suitable bottles are described in detail in U.S. Pat. No. 4,666,065, U.S. Pat. No. 4,696,416, and U.S. Pat. No. 4,981,239.

For uses in targeted next-generation sequencing, the kit can further include primers, adaptors, and other reagents used in or compatible with systems and platforms provided by Agilent Technologies, Inc., Illumina, Inc., 454 Life Sciences, Life Technologies Corporation, Affymetrix, Inc, and others. To that end, one or more of the reaction components for the methods disclosed herein and for next-generation sequencing can be supplied in the form of a kit. In such a kit, an appropriate amount of one or more reaction components is provided in one or more containers or held on a substrate (e.g., by electrostatic interactions or covalent bonding).

A kit containing reagents for performing the methods described herein may include one or more of the components described above. The components may be provided in a variety of forms. For example, the components can be suspended in an aqueous solution or as a freeze-dried or lyophilized powder, pellet, or bead. In the latter case, the components, when reconstituted, form a complete mixture of components for use in an assay.

A kit may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be enriched for the presence of a target nucleic acid can be added to the individual tubes and amplification is carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing a method of the invention. Such substances include, but are not limited to: reagents (including buffers) for lysis of cells or other agents that inhibit unwanted nucleases, control DNA for use in ensuring that components of reactions are functioning properly, DNA fragmenting reagents (including buffers), amplification reaction reagents (including buffers, polymerase, and nucleotides), and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

The container(s) in which the components are supplied can be any conventional container that is capable of holding the supplied form, for instance, microfuge tubes, ampoules, bottles, or integral testing devices, such as fluidic devices, cartridges, lateral flow, or other similar devices. The kits can include either labeled or unlabeled nucleic acid probes/baits for use in enrichment or detection of target nucleic acids. In some embodiments, the kits can further include instructions to use the components in any of the methods described herein. Typical packaging materials for such kits and systems include solid matrices (e.g., glass, plastic, paper, foil, micro-particles and the like) that hold the reaction components or probes in any of a variety of configurations (e.g., in a vial, microtiter plate well, microarray, and the like).

6. ADDITIONAL DEFINITIONS

A "nucleic acid" refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA.

As used herein "bait" or "probe" sequences refer to synthetic long oligonucleotides or oligonucleotides derived from (e.g., produced using) synthetic long oligonucleotides that are complementary to target nucleic acids of interest. In certain embodiments, the set of bait sequences is derived from oligonucleotides synthesized in a microarray and cleaved and eluted from the microarray. In other embodiments, the bait sequences are produced by nucleic acid amplification methods, e.g., using human DNA or pooled human DNA samples as the template.

Bait sequences preferably are oligonucleotides between about 70 nucleotides and 1000 nucleotides in length, more preferably between about 100 nucleotides and 300 nucleotides in length, more preferably between about 130 nucleotides and 230 nucleotides in length and more preferably still are between about 150 nucleotides and 200 nucleotides in length. For selection of exons and other short targets, preferred bait sequence lengths are oligonucleotides of about 40 and 1000, e.g., 100 to about 300 nucleotides, more preferably about 130 to about 230 nucleotides, and still more preferably about 150 to about 200 nucleotides. For selection of targets that are long compared to the length of the capture baits, such as genomic regions, preferred bait sequence lengths are typically in the same size range as the baits for short targets mentioned above, except that there is no need to limit the maximum size of bait sequences for the sole purpose of minimizing targeting of adjacent sequences. Methods to prepare longer oligonucleotides for bait sequences are well known in the art.

As used herein, the term "oligonucleotide" refers to a short polynucleotide, typically less than or equal to 300 nucleotides long (e.g., in the range of 5 and 150, preferably in the range of 10 to 100, more preferably in the range of 15 to 50 nucleotides in length). However, as used herein, the term is also intended to encompass longer or shorter polynucleotide chains. An "oligonucleotide" may hybridize to other polynucleotides, therefore serving as a probe for polynucleotide detection, or a primer for polynucleotide chain extension.

In some embodiments, the bait sequences in the set of bait sequences are RNA molecules. RNA molecules preferably are used as bait sequences since RNA-DNA duplex is more stable than a DNA-DNA duplex, and therefore provides for potentially better capture of nucleic acids. RNA bait sequences can be synthesized using any method known in the art, including in vitro transcription. If RNA is synthesized using biotinylated UTP, single stranded biotin-labeled RNA bait molecules are produced. In preferred embodiments, the RNA baits correspond to only one strand of the double-stranded DNA target. As those skilled in the art will appreciate, such RNA baits are not self-complementary and are therefore more effective as hybridization drivers. In certain embodiments, RNase-resistant RNA molecules are synthesized. Such molecules and their synthesis is well known in the art.

As used herein, the term "target nucleic acid" or "target" refers to a nucleic acid containing a target nucleic acid sequence to be identified. A target nucleic acid may be single-stranded or double-stranded, and often is DNA, RNA, a derivative of DNA or RNA, or a combination thereof. A "target nucleic acid sequence," "target sequence" or "target region" means a specific sequence comprising all or part of the sequence of a single-stranded nucleic acid. A target sequence may be within a nucleic acid template, which may be any form of single-stranded or double-stranded nucleic acid. A template may be a purified or isolated nucleic acid, or may be non-purified or non-isolated.

A target or target nucleic acid usually existing within a portion or all of a polynucleotide, usually a polynucleotide analyte. The identity of the target nucleotide sequence generally is known to an extent sufficient to allow preparation of various probe/bait sequences hybridizable with the target material. The target material usually contains from about 30 to 5,000 or more nucleotides, preferably 50 to 1,000 nucleotides, and more preferably 200 to 500 nucleotides. The target material is generally a fraction of a larger molecule or it may be substantially the entire molecule such as a polynucleotide as described above. The minimum number of nucleotides in the target material is selected to assure that the presence of a target polynucleotide in a sample is a specific indicator of the presence of polynucleotide in a sample. The maximum number of nucleotides in the target material is normally governed by several factors: the length of the polynucleotide from which it is derived, the tendency of such polynucleotide to be broken by shearing or other processes during isolation, the efficiency of any procedures required to prepare the sample for analysis, for example, transcription of a DNA template into RNA, and the efficiency of detection, amplification, or both, of the target nucleotide sequence, where appropriate.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 20" may indicate a range of 18 to 22, and "about 1" may mean from 0.9-1.1. Other meanings of "about" may be apparent from the context, such as rounding off, so, for example "about 1" may also mean from 0.5 to 1.4.

As used herein, the term "contacting" and its variants, when used in reference to any set of components, includes any process whereby the components to be contacted are mixed into the same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

7. EXAMPLE

In this example, the above described hybridization buffers and methods were used to selectively capture and enrich targeted exon regions from human genomic DNA for the analysis of targeted next-generation sequencing.

Briefly, human genomic DNA (gDNA) samples were fragmented and end-modified using methods known in the art. Then, target enrichment via hybridization and amplification was carried out using the fragmented and end-modified gDNA. To that end, a conventional, sodium-based hybridization buffer and two magnesium-based hybridization buffers, Buffer (A) and Buffer (B), were used and compared. The sodium-based hybridization buffer contained 5×SSPE, 5×Denhardt's, 5 mM EDTA, and 0.1% SDS. Buffer (A) included 308 mM $MgCl_2.6H_2O$ and 20 mM Tris (pH 8). Buffer (B) is same as Buffer (A) except that Buffer (B) also included 0.00834% HPMC. Each buffer was prepared from a 5× hybridization buffer concentrate by mixing an appropriate amount concentrate with the DNAs and RNA baits. The 5× buffer concentrate for Buffer (B contained 1540 mM $MgCl_2.6H_2O$, 0.0417%—HPMC, and 100 mM Tris (pH 8).

The hybridizations were carried out using either conventional constant temperature (65° C.) incubation for 24 hours or 1 hour, or using a two-temperature (65° C. and 37° C.) cycling incubation for 1 hour. The profile of this two-temperature cycling incubation is shown in the table below.

| Cycling Profile: Blocking and Fast Hybridization | | |
|---|---|---|
| Step | Cycle # | Temperature and Time |
| Denaturation | 1x | 95° C. for 5 minutes |
| Blocking | pause | 65° C. Pause |

| Cycling Profile: Blocking and Fast Hybridization | | |
|---|---|---|
| Step | Cycle # | Temperature and Time |
| Hybridization | 50-60x | 65° C. for 1 minute |
| | | 37° C. for 3 seconds |
| Storage | 1x | 65° C. hold |

Then, samples of captured DNA from the hybridizations were analyzed by running 1 μl of each sample on the 2100 Bioanalyzer using the DNA1000 assay (Agilent Technologies, Inc.) according to the manufacture's direction. The Bioanalyzer electropherogram profiles are shown in FIGS. 1-4.

Figure 1:
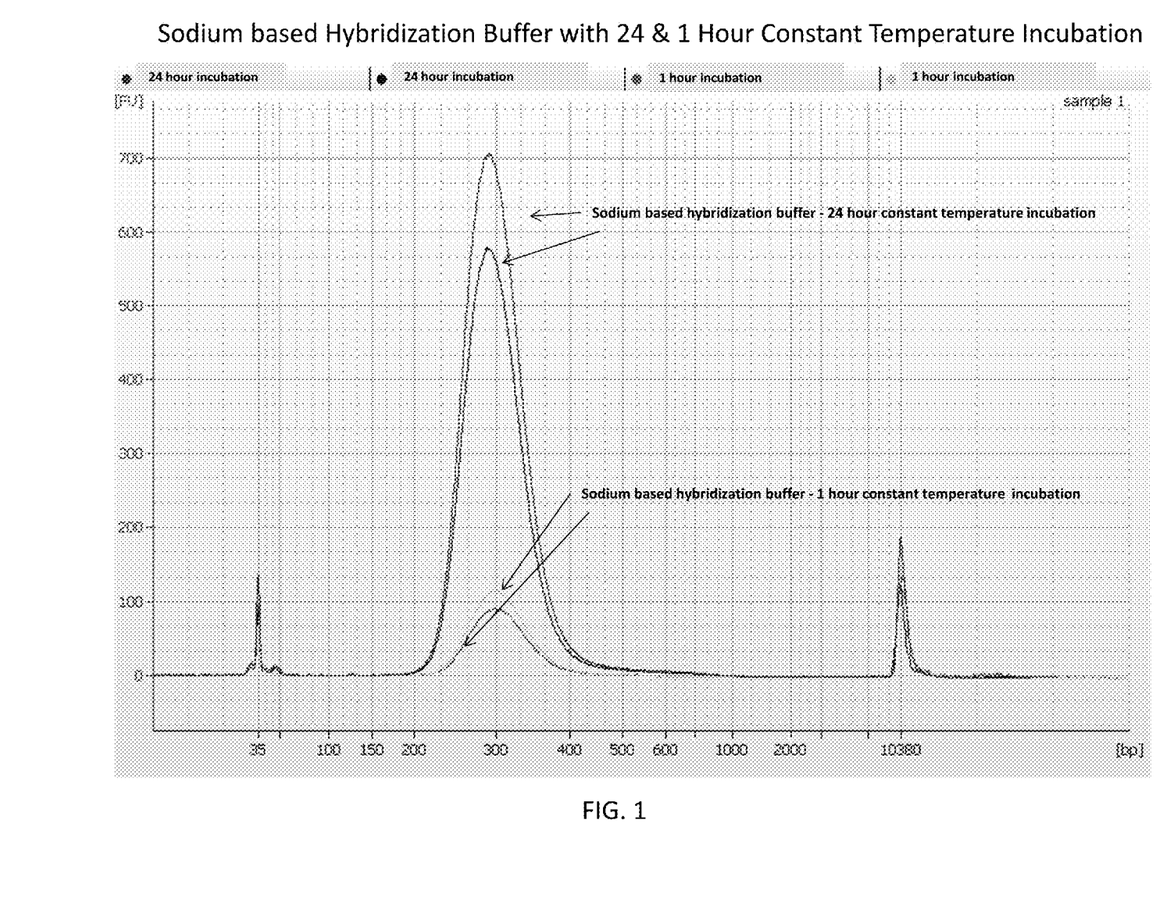
FIG. 1 is a bioanalyzer electropherogram showing conventional sodium-based hybridization buffer's DNA capture performance with 24-hour and 1-hour constant temperature incubations.

As shown in FIG. 1, when the conventional, sodium-based hybridization buffer and constant temperature incubation were used, a much higher amount of gDNAs were captured after a 24-hour incubation as compared those after 1 hour incubation. These results indicated that a longer incubation time (such as 24 hours) is required to obtain satisfactory DNA samples and that a shorter period of time is not desirable when the conventional, sodium-based hybridization buffer is used.

In contrast, when the fast, magnesium-based hybridization Buffer (A) and the two-temperature cycling incubation were used, a 1-hour hybridization resulted in captured gDNA with an mount comparable to or even higher than that obtained after a 24-hour incubation with the conventional, sodium-based hybridization buffer. See FIG. 2. These results indicated that Buffer (A) and cycling incubation procedure are more efficient.

Indeed, when hybridized for 1 hour, Buffer (A) led to much more captured gDNA than the conventional, sodium-based hybridization buffer. And, the two-temperature cycling incubation, when used in connection with the combination the conventional, sodium-based hybridization buffer, also increased the captured gDNA amount, but not to the extent by the fast, magnesium-based hybridization buffer. See FIG. 3.

More surprisingly, when HPMC was included in the hybridization, even more gDNAs were captured. As shown, in FIG. 4, a two-temperature cycling incubation for 1 hour with Buffer (B), which contained HPMC, resulted in captured gDNAs with an mount almost 3 folds as compared to that obtained after a 24-hour incubation with the conventional, sodium-based hybridization buffer. Compared FIGS. 2 and 4. These results indicated that HPMC further increased the capture efficiency.

Figure 5:
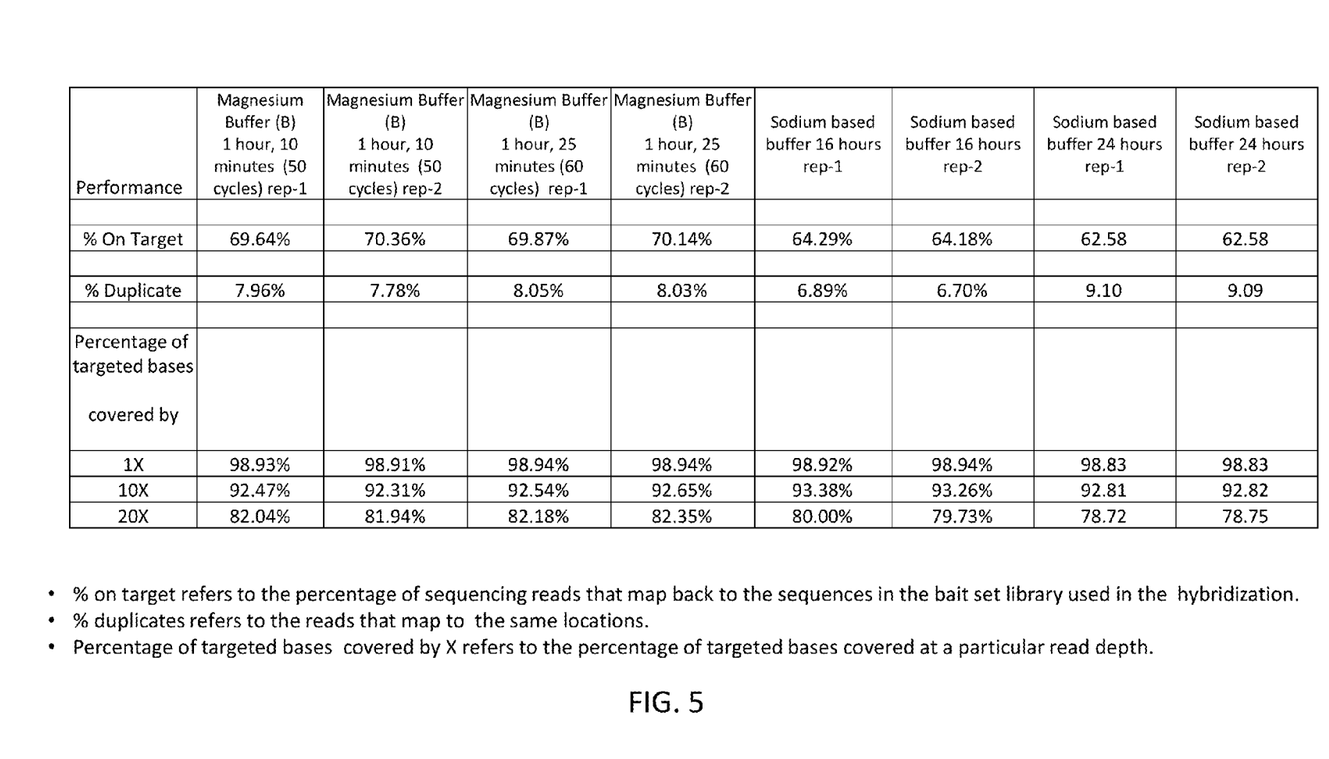
FIG. 5 is a table showing performance parameters of next-generation sequencing using genomic DNAs captured by a fast, magnesium-based hybridization buffer/two-temperature cycling incubation and genomic DNAs captured by a convention approach.

Genomic DNAs captured and enriched using the above described hybridization buffers and incubation profiles were used for next generation sequencing analysis. The resulting performance parameters (On Target rate, Duplicate rate, and Coverage) are presented in the table shown in FIG. 5. It was found that the performance parameters for gDNAs captured using the fast, magnesium-based hybridization Buffer (B) and the two-temperature cycling incubation were comparable to or better than those captured by the convention approach.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated herein in their entireties.

What is claimed is:

1. A composition for nucleic acid hybridization, comprising
a salt of a divalent cation that has a concentration in the range from about 100 mM to about 600 mM,
a buffering agent, wherein said salt and said buffering agent are present in a molar ratio of about 2.5:1 to about 60:1, and
a volume-excluding/thickening agent that (i) is selected from the group consisting of hydroxypropyl methyl cellulose (HPMC), hydroxyethyl methyl cellulose (HEMC), hydroxybutyl methyl cellulose, hydroxypropyl cellulose, methyl cellulose, and hydroxyl methyl cellulose and (ii) has a concentration in the range from about 0.002% to about 0.1% w/w.

2. The composition of claim 1, wherein the buffering agent has a concentration in the range from about 10 mM to about 40 mM.

3. The composition of claim 1, wherein the divalent cation is selected from the group consisting of magnesium, calcium, manganese, cobalt, zinc, and cadmium.

4. The composition of claim 1, wherein the buffering agent is selected from the group consisting of Tris, HEPES, TAPS, Tricine, Bicine, Bis-Tris, NaOH, KOH, TES, EPPS, and MOPS.

5. The composition of claim 1, wherein the divalent cation is magnesium.

6. The composition of claim 5, wherein the salt is $MgCl_2$, the volume-excluding/thickening agent is HPMC, and the buffering agent is Tris.

7. The composition of claim 6, wherein said salt has a concentration of about 308 mM, said HPMC has a concentration of about 0.00834%, and said buffering agent has a concentration of about 20 mM.

8. The composition of claim 1, wherein the pH of the composition is about 7-7.

9. A buffer concentrate for preparing a hybridization solution, wherein dilution of said buffer concentrate by a factor ranging from 2-fold to 20-fold yields the composition of claim 1.

10. The buffer concentrate of claim 9, wherein dilution of said buffer concentrate by a factor of 5-fold yields said composition.

11. A kit for nucleic acid hybridization, comprising the buffer concentrate of claim 9 and packaging material therefor.

* * * * *

UNITED STATES PATENT AND TRADEMARK OFFICE
CERTIFICATE OF CORRECTION

PATENT NO. : 10,093,962 B2
APPLICATION NO. : 14/868961
DATED : October 9, 2018
INVENTOR(S) : Michael Borns Page 1 of 1

It is certified that error appears in the above-identified patent and that said Letters Patent is hereby corrected as shown below:

In the Specification

In Column 2, Line 50, delete "methycellulose," and insert -- methyl cellulose, --, therefor.

In Column 7, Line 35, delete "methycellulose," and insert -- methyl cellulose, --, therefor.

In Column 8, Line 43, delete "-2,2dimethylpropane," and insert -- -2,2-dimethylpropane, --, therefor.

In Column 8, Line 45, delete "2-amino4,6-" and insert -- 2-amino-4,6- --, therefor.

In Column 8, Line 46, delete "2-amino4-" and insert -- 2-amino-4- --, therefor.

In Column 8, Line 46, delete "6-hydroxy4-" and insert -- 6-hydroxy-4- --, therefor.

In Column 12, Line 19, after "µL" delete "A".

In the Claims

In Column 20, Line 47, in Claim 8, delete "7-7." and insert -- 7-11. --, therefor.

Signed and Sealed this
Fifth Day of February, 2019

Andrei Iancu
*Director of the United States Patent and Trademark Office*